United States Patent
Li et al.

(10) Patent No.: US 8,409,274 B2
(45) Date of Patent: Apr. 2, 2013

(54) TECHNIQUES FOR ATTACHING FLEXIBLE LEAFLETS OF PROSTHETIC HEART VALVES TO SUPPORTING STRUCTURES

(75) Inventors: XueMei Li, Shoreview, MN (US); Yi-Ren Woo, Woodbury, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 233 days.

(21) Appl. No.: 11/796,471

(22) Filed: Apr. 26, 2007

(65) Prior Publication Data
US 2013/0018456 A1    Jan. 17, 2013

(51) Int. Cl.
*A61F 2/24* (2006.01)
(52) U.S. Cl. .......................... 623/2.17; 623/2.1
(58) Field of Classification Search ............ 623/2.1, 623/2.17, 2.38, 1.15, 1.24, 2.11–2.15, 2.41, 623/2.18; 606/151
See application file for complete search history.

(56) References Cited

U.S. PATENT DOCUMENTS

| | | | | |
|---|---|---|---|---|
| 4,506,394 A * | 3/1985 | Bedard | ........................ | 623/2.38 |
| 5,037,434 A | 8/1991 | Lane | | |
| 5,147,391 A | 9/1992 | Lane | | |
| 5,910,170 A * | 6/1999 | Reimink et al. | ............. | 623/2.38 |
| 6,102,944 A * | 8/2000 | Huynh et al. | ................. | 623/2.14 |
| 6,338,740 B1 * | 1/2002 | Carpentier | .................... | 623/2.13 |
| 6,461,382 B1 * | 10/2002 | Cao | .............................. | 623/2.19 |
| 6,530,952 B2 * | 3/2003 | Vesely | .......................... | 623/2.18 |
| 6,558,418 B2 * | 5/2003 | Carpentier et al. | .......... | 623/2.14 |
| 6,719,789 B2 | 4/2004 | Cox | | |
| 7,201,771 B2 * | 4/2007 | Lane | ............................ | 623/2.14 |
| 2002/0173842 A1 | 11/2002 | Buchanan | | |
| 2004/0078074 A1 * | 4/2004 | Anderson et al. | ............. | 623/2.11 |
| 2004/0193261 A1 * | 9/2004 | Berreklouw | ................. | 623/2.11 |
| 2006/0135964 A1 | 6/2006 | Vesely | | |
| 2006/0136052 A1 * | 6/2006 | Vesely | .......................... | 623/2.18 |
| 2006/0235508 A1 * | 10/2006 | Lane et al. | ..................... | 623/2.4 |
| 2008/0228264 A1 | 9/2008 | Li et al. | | |

FOREIGN PATENT DOCUMENTS

| | | |
|---|---|---|
| EP | 0179562 A1 | 4/1986 |
| WO | 0018333 A1 | 4/2000 |

OTHER PUBLICATIONS

International Search Report for Application No. PCT/US2008/005045 dated Jul. 31, 2008.

* cited by examiner

*Primary Examiner* — Thomas J Sweet
*Assistant Examiner* — Matthew Schall
(74) *Attorney, Agent, or Firm* — Lerner, David, Littenberg, Krumholz & Mentlik, LLP (57) ABSTRACT

A prosthetic heart valve has an annular valve-perimeter-shape-defining structure having a radially outer surface. A clip structure is provided on the outer surface. This clip structure is used to attach flexible valve leaflets to the shape-defining structure. One or more retainer members may be used to help hold the leaflets in the clip structure.

33 Claims, 8 Drawing Sheets

TECHNIQUES FOR ATTACHING FLEXIBLE LEAFLETS OF PROSTHETIC HEART VALVES TO SUPPORTING STRUCTURES

BACKGROUND OF THE INVENTION

This invention relates to prosthetic heart valves of the type that include flexible leaflets and a structure for supporting those leaflets.

Prosthetic heart valves that include flexible leaflets and a structure for supporting those leaflets are well known. Such heart valves typically require some means for securing the leaflets to the support structure. The most common means for doing this is suturing. The suturing process tends to be labor-intensive, and the quality of the result may depend on the skill-level of the individual operator. Suturing perforates the leaflet material and can potentially cause stress concentration, especially when placed at a location that experiences large operational stress. The tension applied by the suture may not be well controlled, which can affect the local geometry of the leaflet at the location of suture attachment. All of these factors may adversely affect the service life of the device.

SUMMARY OF THE INVENTION

In accordance with this invention, a prosthetic heart valve includes an annular valve-perimeter-shape-defining structure having a radially outer surface. A clip structure is provided on this outer surface. The clip structure is used to attach flexible valve leaflets to the shape-defining structure. One or more retainer members may be used to help the clip structure hold onto the leaflets. Sewing cuff and/or cover structures may be provided on the valve.

Further features of the invention, its nature and various advantages, will be more apparent from the accompanying drawings and the following detailed description.

DETAILED DESCRIPTION

Figure 1:
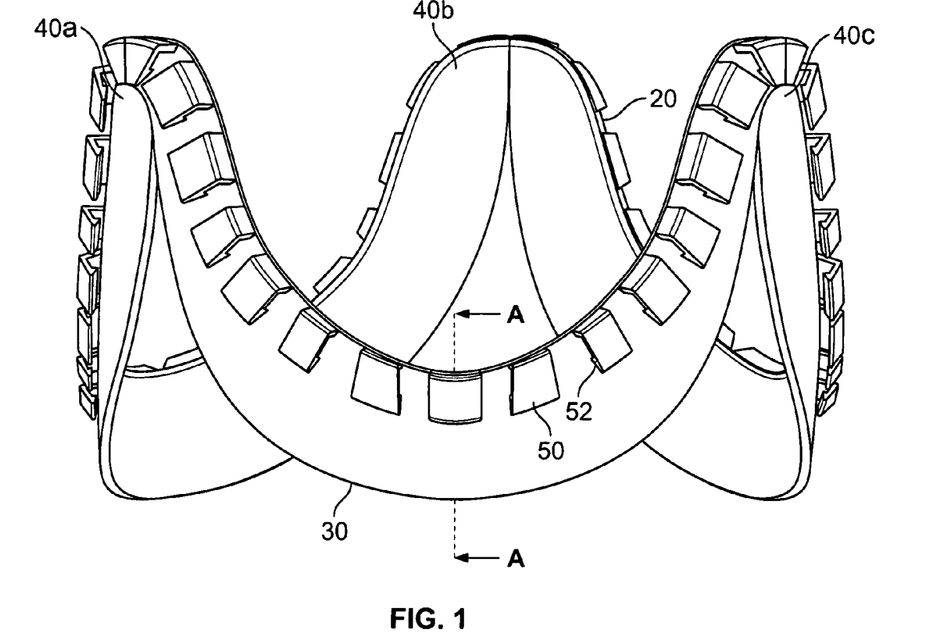
FIG. 1 is a simplified elevational view of an illustrative prosthetic heart valve leaflet support structure in accordance with the invention.

FIG. 1 shows an illustrative embodiment of a prosthetic heart valve leaflet support structure 10 in accordance with the invention. FIG. 1 is similar to a FIG. in commonly assigned, co-pending, Li et al. U.S. patent application Ser. No. 11/717,305, filed Mar. 12, 2007, which is hereby incorporated by reference herein in its entirety. However, structure 10 is used differently in the present invention than in the Li et al. reference.

Structure 10 is a hollow, annular structure that may sometimes be referred to as a stent. Structure 10 may be made of any of several biologically compatible materials such as certain metals or plastics. Structure 10 may have any of a range of structural strengths, from rigid or substantially rigid at one extreme to flexible or relatively flexible at the other extreme. Structure 10 is a continuous, hollow annulus. Structure 10 has an upper edge 20, which undulates up and down as one proceeds annularly around the structure. Upper edge 20 is typically adjacent the blood-outflow end of a prosthetic heart valve that includes structure 10. Structure 10 has a lower edge 30, which also undulates up and down as one proceeds annularly around the structure. Lower edge 30 is typically adjacent the blood-inflow end of a prosthetic heart valve that includes structure 10. The three relatively high portions of structure 10 (directed upward as viewed in FIG. 1) may be referred to as the commissure regions 40a-c of the valve. Commissure regions 40 are equally spaced from one another around the valve.

The upper portion of structure 10 has a plurality of clips 50 that project radially out from the main body of the structure. Clips 50 are spaced from one another in the annular direction around structure 10, and in this illustrative embodiment they are distributed all the way around the upper portion of structure 10. Each clip 50 opens in the direction that is generally downward and away from the adjacent portion of the upper edge 20 of structure 10. The detailed shape of each clip 50 will be better seen in some of the later FIGS. For the present it will suffice to point out that the free edge or end of each clip 50 has a latch component or surface 52 that projects from the rest of the clip back toward the adjacent outer surface of the main body of structure 10.

Figure 2:
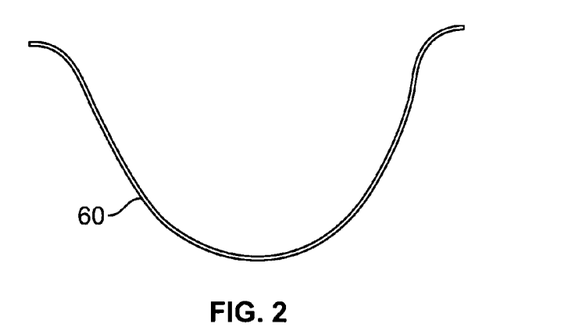
FIG. 2 is a simplified elevational view of an illustrative embodiment of a component that can be used with the FIG. 1 structure in accordance with the invention.
Figure 3A:
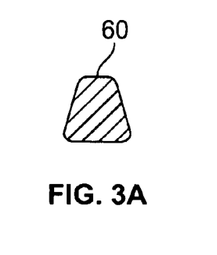
FIG. 3 shows three examples of cross sections that the FIG. 2 component can have in accordance with the invention.
Figure 3B:
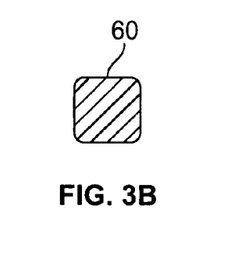
Figure 3C:
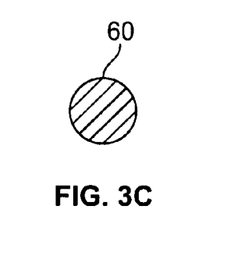

Flexible valve leaflet material (not shown in FIG. 1, but shown in several later FIGS.) is attached to structure 10 as will now be described. Typically three separate sheets of such material are used. Each sheet is used so that it extends between a respective pair of two annularly adjacent commissure regions 40. In particular, one sheet is used between commissure regions 40a and 40b; a second sheet is used between commissure regions 40b and 40c; and the third sheet is used between commissure regions 40c and 40a. An edge portion of each sheet is folded over an associated retainer member 60 like the representative one shown in FIG. 2. Each retainer member 60 may be a wire or a wire-like member. Each retainer member 60, with the associated leaflet sheet folded over it as described above, is then pushed into the clips 50 between two of the annularly adjacent commissure regions 40. The latch elements 52 on clips 50 prevent the retainer member 60 and associated leaflet material from coming back out of clips 50. Accordingly, this structure permanently secures the leaflets to support structure 20. Some illustrative cross sections for member 60 are shown in FIG. 3 and include (a) a trapezoid (preferably with somewhat rounded corners), (b) a square (again, preferably with somewhat rounded corners), and (c) a circle. Note that in the illustrative embodiment shown in FIG. 2, retainer member 60 is representative of one of three such members that are used. Each such retainer member 60 is long enough to extend substantially continuously between a respectively associated pair of two adjacent ones of commissure regions 40.

The main portion of each leaflet that extends out from clips 50 runs down along the outer surface of the lower portion of structure 10 and is deflected around the lower edge 30 of that structure into the interior of the structure. There the three leaflets come together (meet) in a flexible way to provide a valve structure that can be either closed (leaflets together; blood flow in the outflow-to-inflow direction prevented) or open (leaflets somewhat spaced apart; blood flow in the inflow-to-outflow direction permitted). The leaflets are shaped so that they conform to all of these geometric parameters. The leaflets naturally respond to greater blood pressure on the inflow side by opening as described above. Conversely, the leaflets naturally respond to greater blood pressure on the outflow side by closing as described above.

Figure 4:
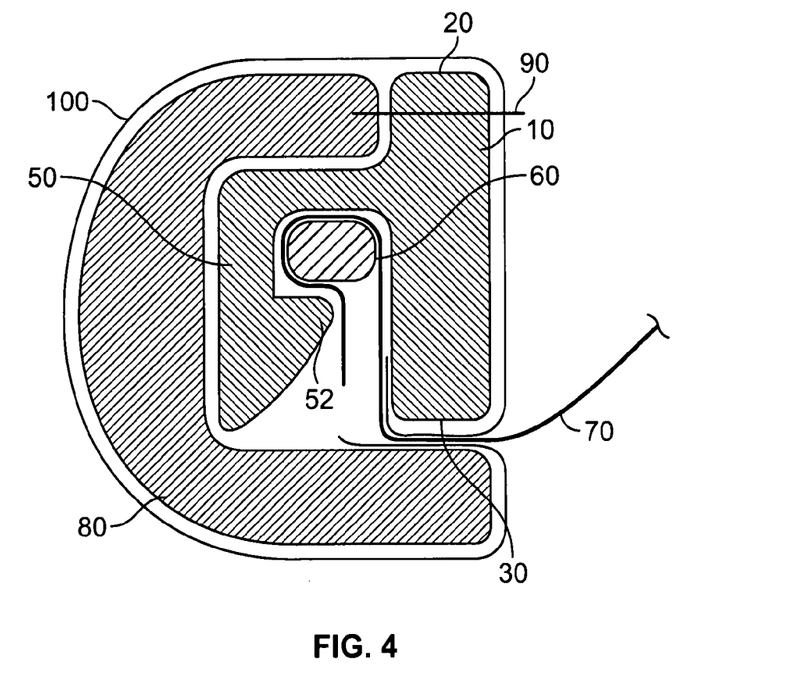
FIG. 4 is a simplified cross sectional view of an illustrative finished valve in accordance with the invention, which view may be taken in the area generally indicated at A-A in FIG. 1 (but with more components added to what is shown in FIG. 1).

FIGS. 4-9 and 15 show some examples of some additional constructional details that can be used. Each of these FIGS. is a sectional view somewhat like section A-A in FIG. 1, although deviating from such a section to show various possible alternatives and additional components. FIG. 4 shows how the edge portion of representative leaflet 70 goes up into the recess in representative clip 50, where it is folded or wrapped around representative retainer member 60. FIG. 4 also shows how the latch portion 52 of clip 50 helps prevent the edge of leaflet 70 and retainer member 60 from coming out of the clip after those components 60 and 70 have been pushed up into the clip. The lower side of latch portion 52 is inclined down and away from the adjacent outer surface of the main body of structure 10 so that components 60 and 70 can cam open clip 50 when they are pushed up into the clip. After components 60 and 70 have moved up past latch portion 52, the clip can resiliently return to the FIG. 4 condition, in which latch portion 52 prevents components 60 and 70 from moving back down out of the clip.

FIG. 4 further illustrates the path that leaflet 70 follows outside of clip 50, i.e., down from the clip, around the blood-inflow edge 30 of structure 10, and into the interior space surrounded by that structure.

FIG. 4 still further illustrates that the radially outer portion of structure 10 may be covered by a relatively thick pad 80 of material that can be used as a sewing cuff for enabling the surgeon who is using the prosthetic valve to suture the valve into the patient who is receiving the prosthesis. Any of a range of sewing cuff constructions can be used for pad 80. For example, several materials and constructions are known for sewing cuffs, and these known materials/constructions can be used for pad 80. As is traditional for known sewing cuffs, pad 80 should be easily penetrated by a suture needle and suture material, and should thereafter hold the suture material without risk of that material tearing out. Pad 80 may be held to structure 10 by sutures, e.g., as shown at 90.

FIG. 4 still further shows that at least a substantial portion of the otherwise exposed surfaces of components 10 and 80 may be covered by another layer of material 100 such as fabric. Layer 100 may be secured to the other components by any suitable means such as by sutures 90.

Figure 5:
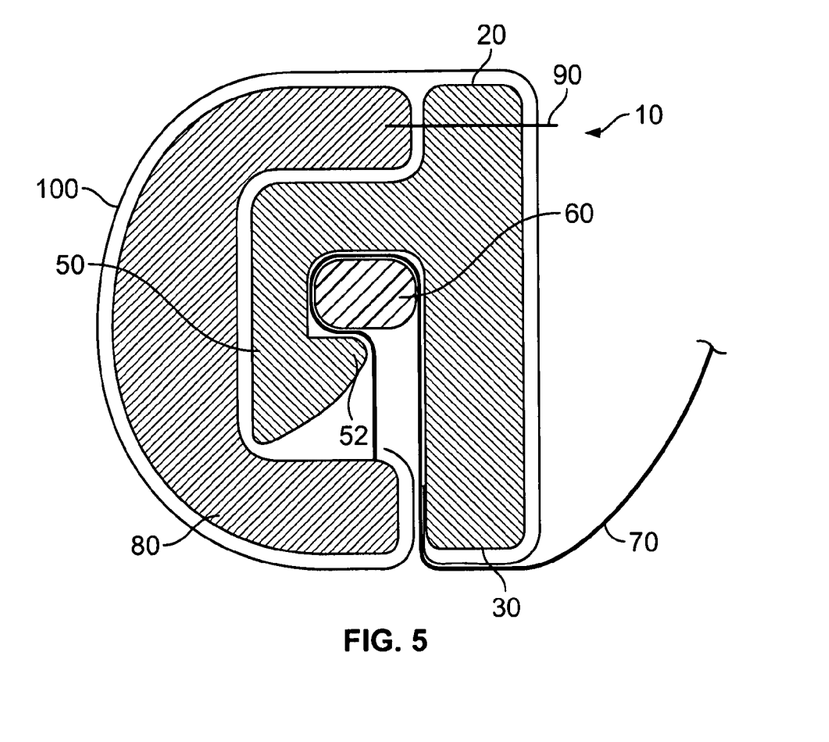
FIG. 5 is generally similar to FIG. 4 for another illustrative embodiment in accordance with the invention.

FIG. 5 shows an alternative embodiment of what is shown in FIG. 4. Features in FIG. 5 that are closely similar to what is shown in FIG. 4 will not need to be described again. The biggest difference between FIG. 4 and FIG. 5 is that whereas in FIG. 4 pad 80 extends down over inflow edge 30, in FIG. 5 the lower-most part of pad 80 is approximately in the same plane as inflow edge 30.

Figure 6:
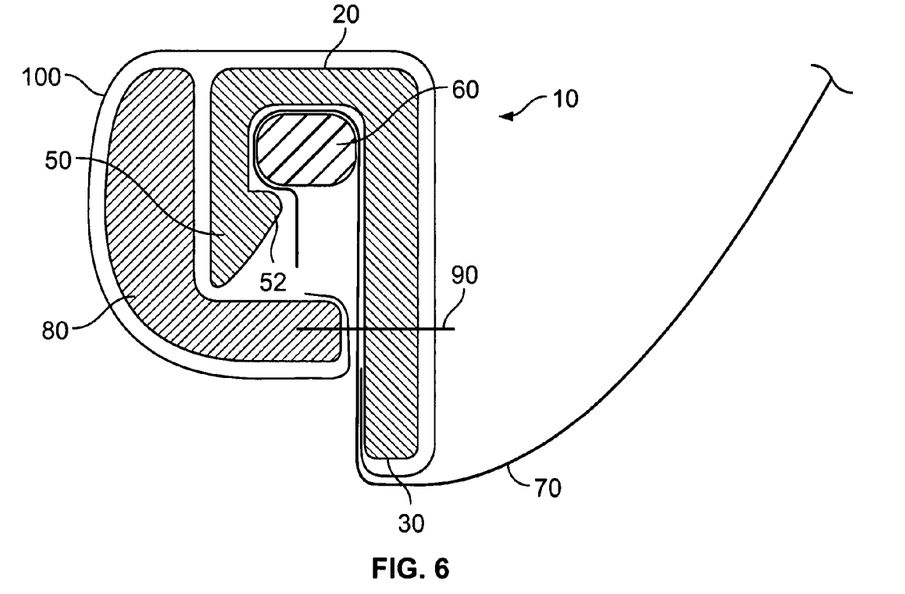
FIG. 6 is again generally similar to FIGS. 4 and 5 for another illustrative embodiment in accordance with the invention.

FIG. 6 shows another alternative to what is shown in FIGS. 4 and 5. Features in FIG. 6 that are closely similar to what is shown in FIGS. 4 and 5 will not need to be described again. The cross-sectional shape of structure 10 in FIG. 6 is very close to what is shown in FIG. 1. Thus in FIG. 6 clips 50 come off of the main body of structure 10 at or very close to outflow edge 20. Pad 80 covers clips 50, but pad 80 does not extend all the way down to inflow edge 30.

Figure 7:
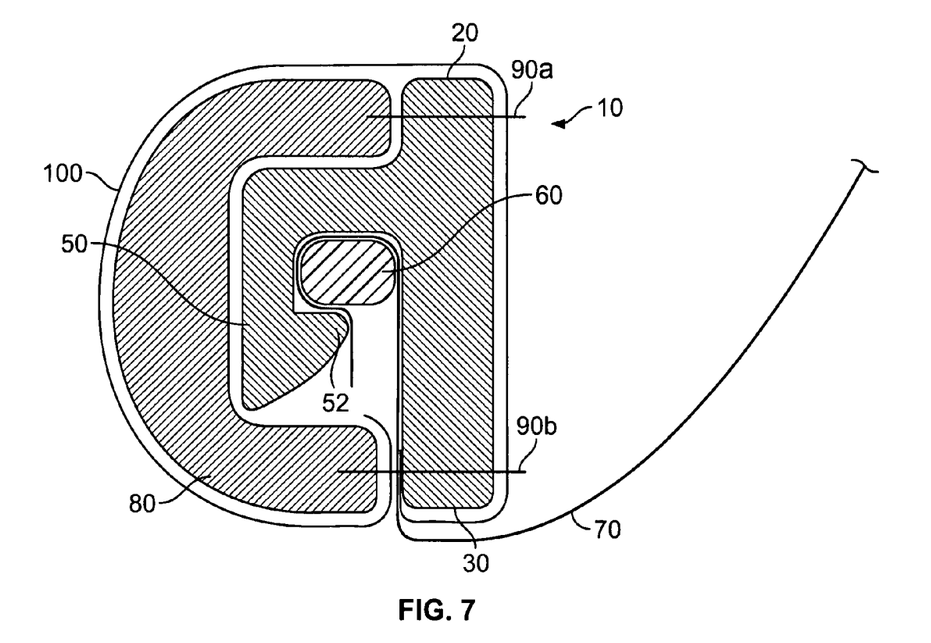
FIG. 7 is once again similar to FIGS. 4-6 for another illustrative embodiment in accordance with the invention.

FIG. 7 shows yet another alternative to what is shown in FIGS. 4-6. Features in FIG. 7 that are similar to what is shown in FIGS. 4-6 will not be described again. In FIG. 7 pad 80 covers clips 50, starting from approximately the plane of outflow edge 20 and extending to approximately the plane of inflow edge 30. Sutures at two locations 90a and 90b (respectively near outflow edge 20 and inflow edge 30) can be used to hold elements 10, 80, and 100 together.

Figure 8:
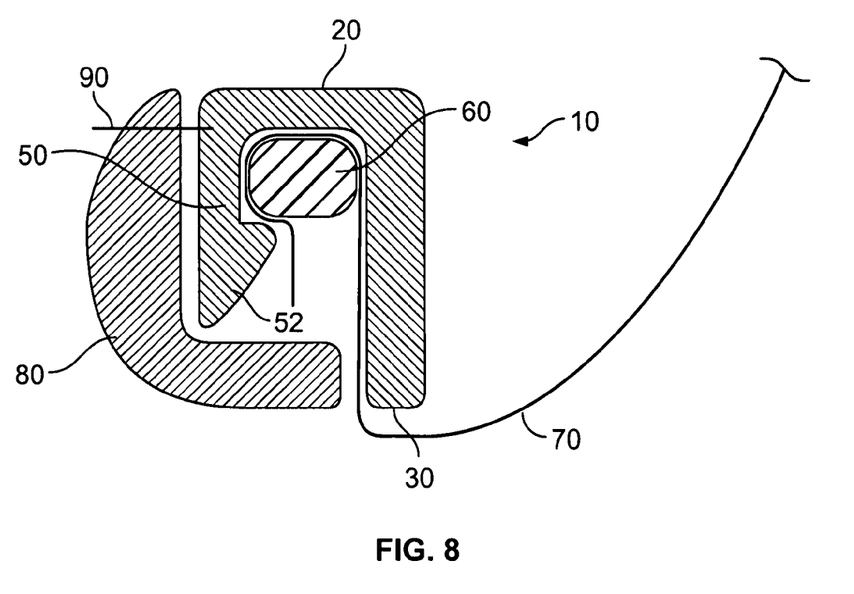
FIG. 8 is again similar to FIGS. 4-7 for yet another illustrative embodiment of the invention.

FIG. 8 shows still another alternative to what is shown in FIGS. 4-7. FIG. 8 is somewhat like FIG. 6, but shows an alternative location for sutures 90, and also inflow edge 30 closer to the bottom of pad 80.

Figure 9:
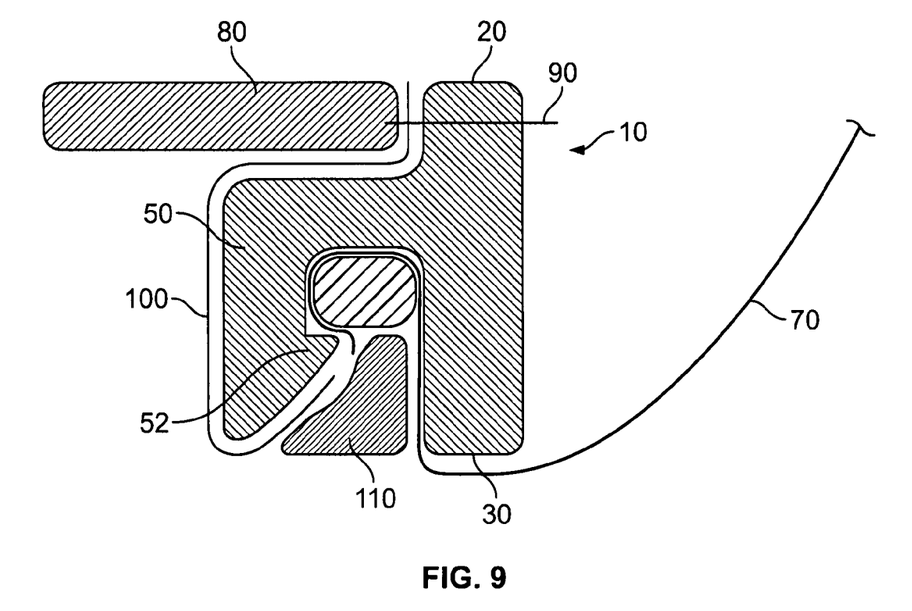
FIG. 9 is again similar to FIGS. 4-8 for still another illustrative embodiment of the invention.

FIG. 9 shows yet another alternative to what is shown in FIGS. 4-8. In FIG. 9 sewing cuff 80 is largely in a plane near blood-outflow edge 20. The upper edge of cover 100 is captured between sewing cuff 80 and the upper portion of structure 10. The lower portion of cover 100 may be captured using clip 50. The gap between the lower portion of clip 50 and the adjacent outer surface of structure 10 can be filled by a filler member 110. Alternatively this gap can be designed to be very small.

Figure 15:
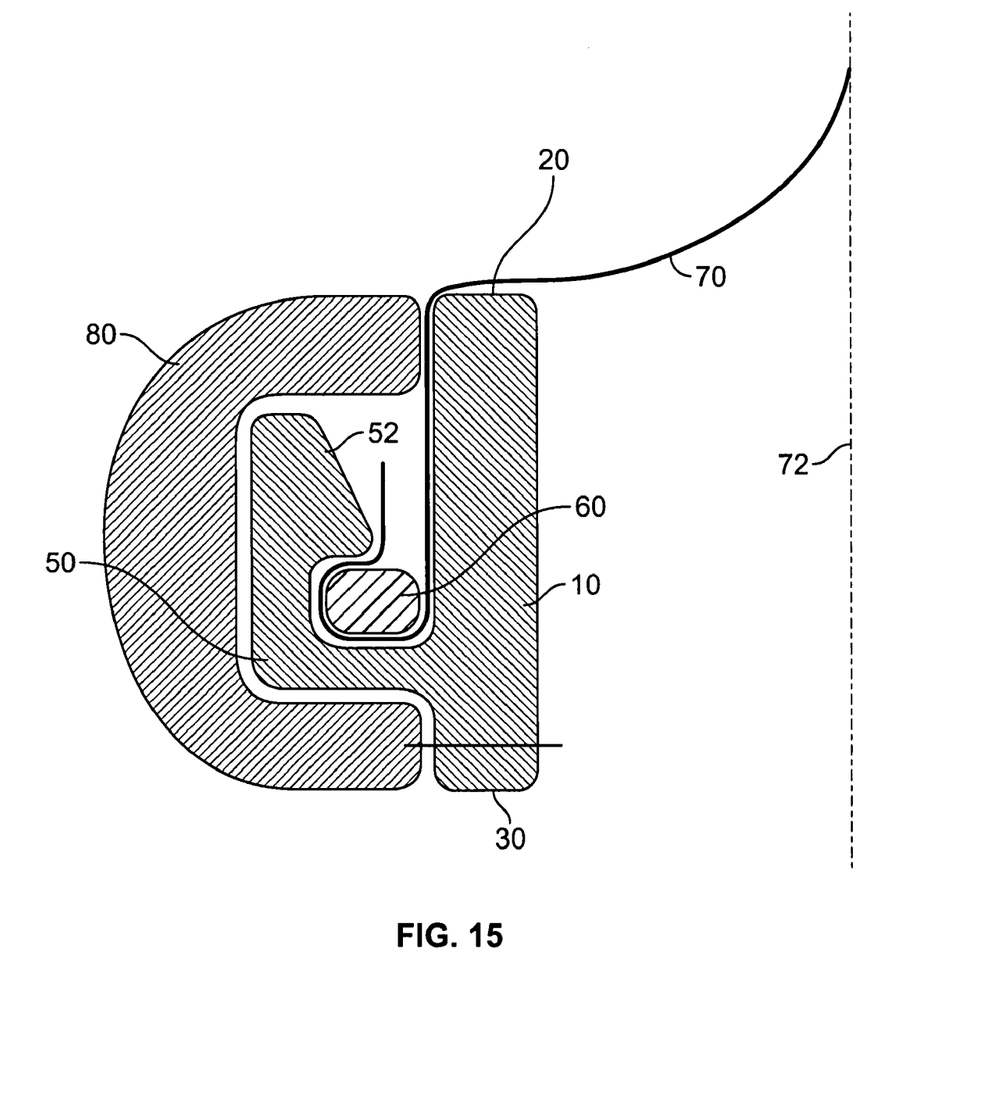
FIG. 15 is again similar to FIGS. 4-9 for yet another illustrative embodiment of the invention.

FIG. 15 shows still another alternative to what is shown in FIGS. 4-9. FIG. 15 is illustrative of embodiments in which clip 50 is open toward the blood-outflow edge 20 (rather than toward the blood-inflow edge 30 as in FIGS. 4-9) of structure 10. (See also FIG. 11 for this type of clip orientation.) Thus in FIG. 15, leaflet 70 extends from clip structure 50, over blood-outflow edge 20, and toward a central axis 72 about which structure 10 is annular.

Figure 10:
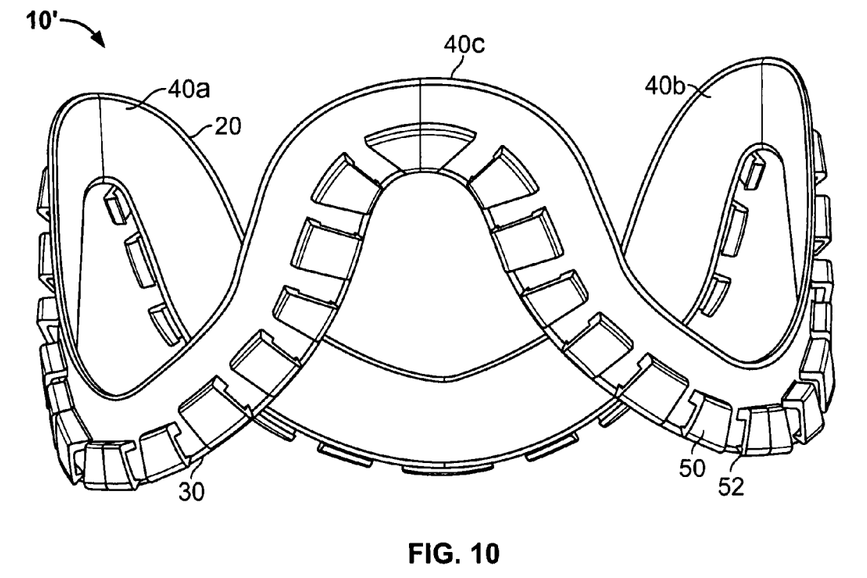
FIG. 10 is similar to FIG. 1 for another illustrative embodiment of the invention.

FIG. 10 illustrates the point that clips 50 do not have to be at or near the blood-outflow edge 20 of structure 10. In the alternative embodiment shown in FIG. 10, clips 50 are instead near the blood-inflow edge 30 of structure 10'. This general type of embodiment is also illustrated by FIGS. 4 and 9.

Figure 11:
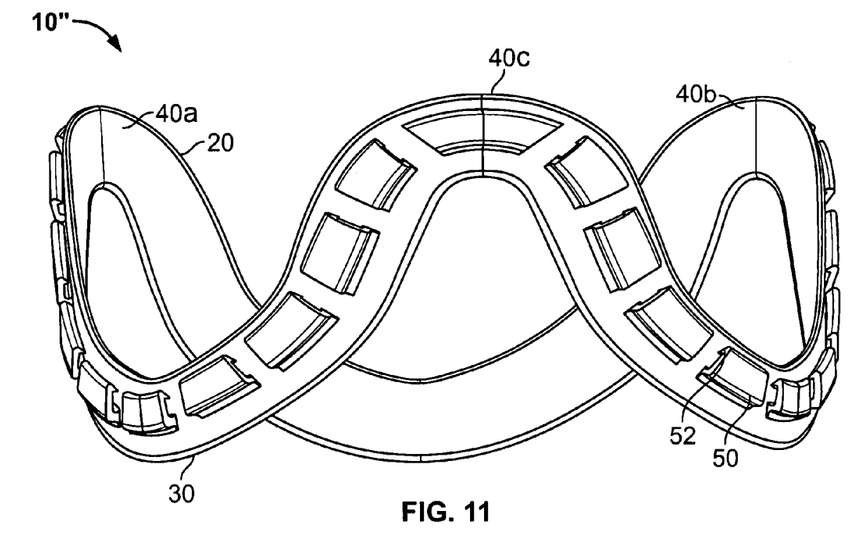
FIG. 11 is similar to FIGS. 1 and 10 for yet another illustrative embodiment of the invention.

Still other possible alternatives are illustrated by FIG. 11. In the FIG. 11 embodiment, clips 50 are approximately midway between the blood-outflow edge 20 and the blood-inflow edge 30 of structure 10". In addition, FIG. 11 shows the alternative of having clips 50 open toward blood-outflow edge 20, rather than opening toward the blood-inflow edge 30 as in the earlier-described embodiments. With clips 50 opening toward blood outflow edge 20, retainer member 60 with leaflet material 70 folded around it will be inserted into clips 50 from the direction of outflow edge 20, rather than from the direction of inflow edge 30. The main portion of such a leaflet that extends from clips 50 will pass up and over outflow edge 20 and will be deflected inwardly toward central longitudinal axis 72 as shown, for example, in FIG. 15.

Figure 12:
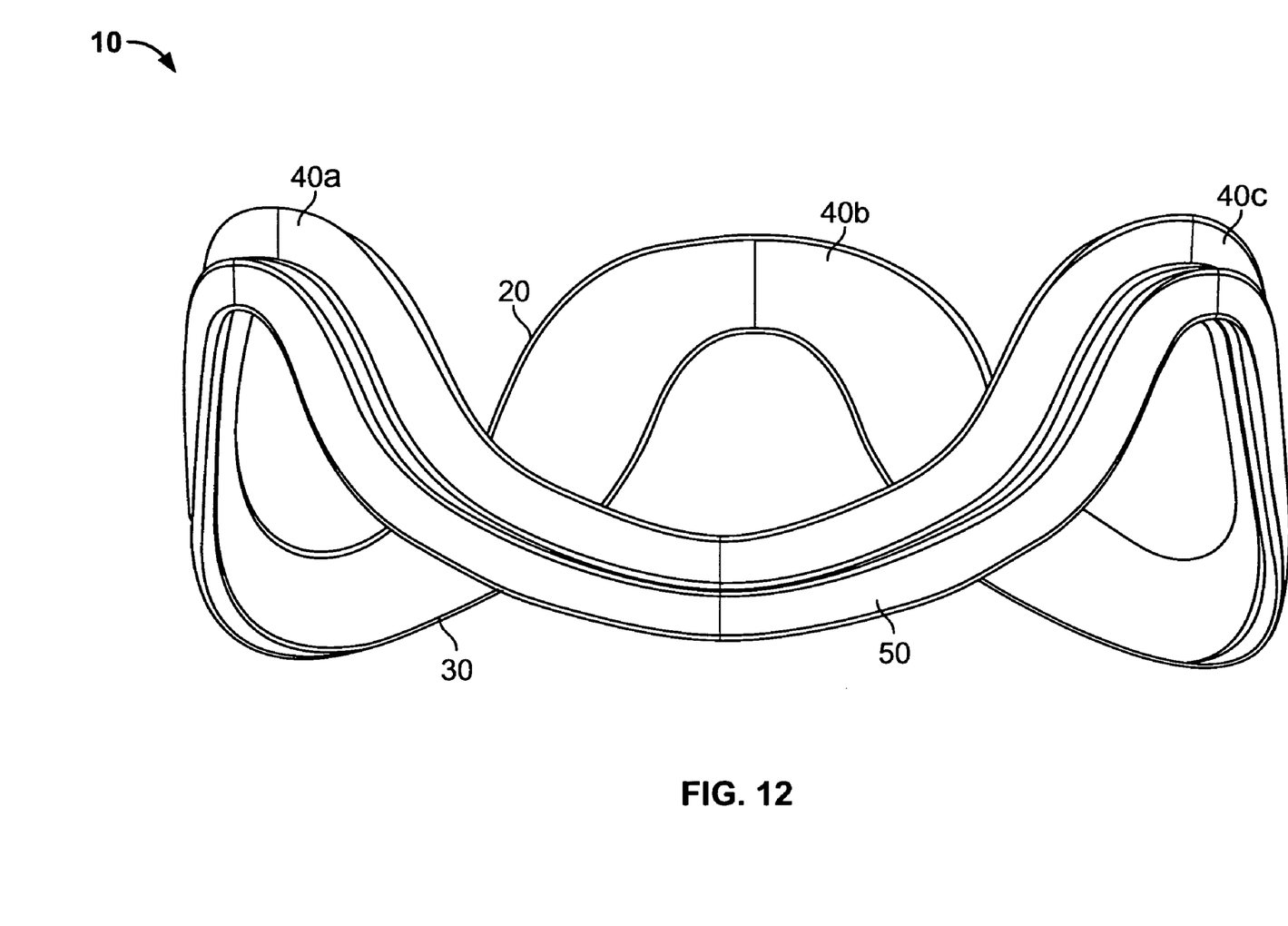
FIG. 12 is similar to FIGS. 1, 10, and 11 for still another illustrative embodiment of the invention.

Up to this point, all of the embodiments that have been shown have used a plurality of clips 50 that are spaced from one another as one proceeds annularly around structure 10/10'/10". (For convenience, all versions of structures like 10, 10', and 10" may be referred to using the generic reference number 10.) FIG. 12 illustrates an alternative to this in which a more continuous clip structure 50 is used. In other respects FIG. 12 may be like FIG. 10. At any point along its length (in the annular direction around structure 10), more continuous clip structure 50 (FIG. 12) may have a cross section like any of the cross sections shown and described earlier in this specification. More continuous clip structure 50 may be completely continuous annularly around structure 10, or it may be interrupted at one or more locations around structure 10. Even if the clip structure 50 is actually made up of several segments (as it is, for example, FIGS. 1, 10, and 11), the number, distribution (spacing), and extent of these segments are preferably such that the clip segments between two adjacent commissure regions 40 collectively occupy more than half of the distance between those commissure segments.

Figure 13:
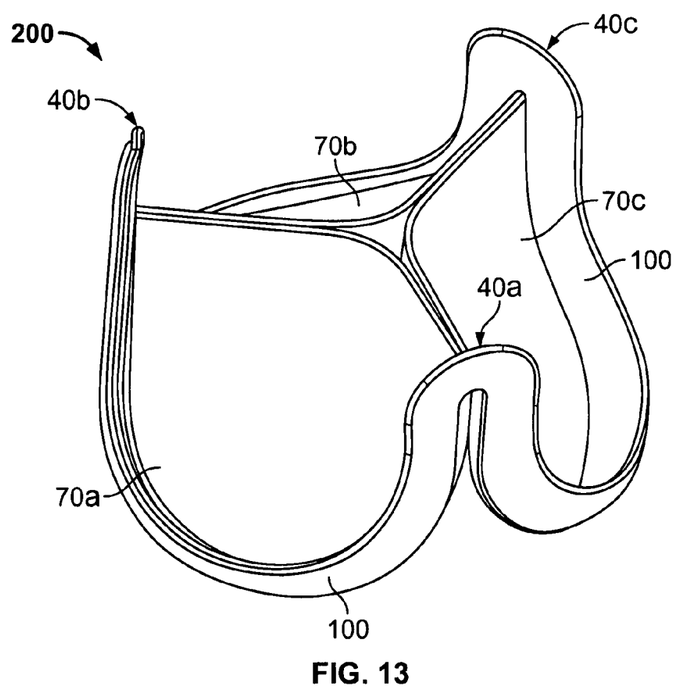
FIG. 13 is a simplified perspective or isometric view of an illustrative embodiment of a finished prosthetic heart valve in accordance with the invention.

FIG. 13 shows an illustrative finished heart valve 200 in accordance with the invention. In FIG. 13, the above-described details as to how the edges of leaflets 70 are secured are largely obscured by the presence of cover 100. It will be understood, however, that the structure under cover 100 may be similar to what is shown in any of the other FIGS. (with the possible exception of FIGS. 11 and 15, which would typically be used for embodiments in which the leaflets enter the interior of the valve by passing over the upper edge 20 of structure 10 rather than by passing over the lower edge 30 of that structure as in FIG. 13). Note in FIG. 13 that when the valve is closed, the free edges of the three leaflets 70a-c meet in the interior of the valve (i.e., in the area or volume that is surrounded in at least a general way by the remaining structure of the valve). These "co-apting" portions of the leaflets separate from one another to allow blood to pass through the valve when the blood pressure on the inflow side is greater than the blood pressure on the outflow side. (The inflow side is down in FIG. 13. The outflow side is up in FIG. 13.)

Figure 14:
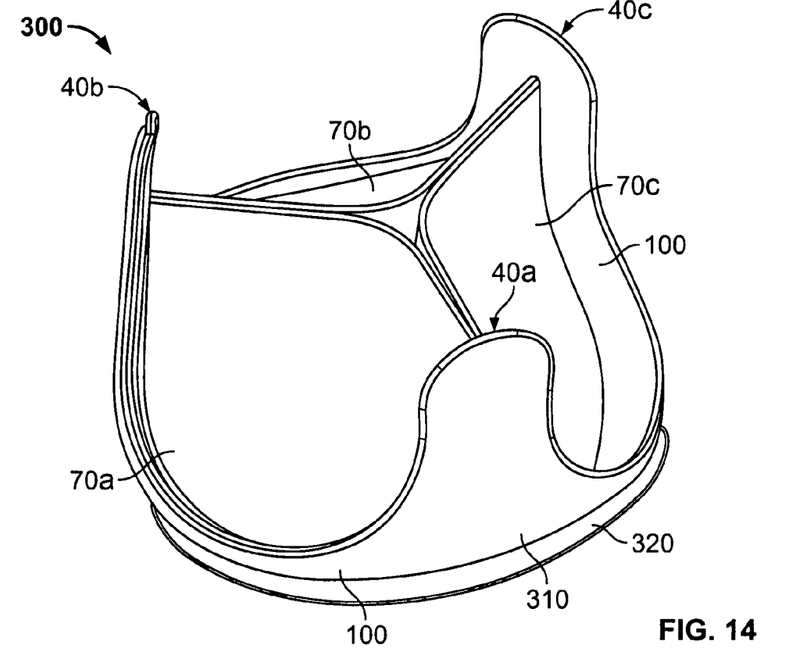
FIG. 14 is similar to FIG. 13 for another illustrative embodiment of a finished prosthetic heart valve in accordance with the invention.

FIG. 14 shows another illustrative embodiment of a heart valve 300 in accordance with the invention. FIG. 14 may be generally similar to FIG. 13, except that in FIG. 14 sewing cuff 320 follows a path annularly around the valve that is less undulating than the outflow edge of the valve. In addition, any portion of the valve perimeter that would otherwise be open between the outflow edge and sewing cuff 320 is covered or closed by additional material 310 (which can be part of cover 100 or the like). FIG. 14 thus illustrates the point that the sewing cuff can follow a path around the valve that is different than the paths of other structures around the valve, and that material of the cover or the like can be used to close any openings that would otherwise appear in the radially outer perimeter of the valve.

As a matter of overall recapitulation, structure 10 is typically the component of a valve of this invention that is principally responsible for giving the valve its outer perimeter shape (at least in the absence of significant other forces being applied to the valve). For example, this outer perimeter shape may be basically circular in plan view (although other plan view shapes are also possible). Other aspects of the outer perimeter shape that structure 10 imparts to the valve may be features like the undulating blood-inflow and blood-outflow edges described earlier. Structure 10 may therefore be referred to as the perimeter-shape-defining component of the valve. Structure 10 may be rigid or substantially rigid, or it may be flexible to any desired degree (consistent with the characteristic of giving the outer perimeter of the valve a particular shape in the absence of significant other forces). Structure 10 may be made of any suitable material such as metal or polymer (e.g., titanium, Nitinol, polyetheretherketone (PEEK), or acetals). Structure 10 may be solid or perforated material, or it may be assembled from a plurality of subcomponents.

Retainer member 60 may be a wire-like or strand-like member, e.g., of Elgiloy, Nitinol, stainless steel, PEEK, or a ceramic.

Leaflets 70 are typically made of a flexible, sheet-like material. The following are some examples of flexible materials that are suitable for use as leaflets: (1) materials derived from animal or human tissue (e.g., pericardium, heart valve, venous valve, dura mater, small intestine submucosa, etc.), (2) biologically synthesized or tissue-engineered materials (e.g., collagen, fibroblast populated matrix, stem cell populated scaffold, endothelial cell seeded material, etc.), and (3) polymeric materials (e.g., silicone, polyurethane, styrene-isobutylene-styrene block copolymer, polymer-impregnated fabric mesh, etc.).

It will be appreciated that use of the present invention can avoid or reduce the need for sutures to attach leaflets 70 to supporting structure like 10. If any sutures continue to be used, they penetrate the leaflets at fewer locations and/or they can be placed at locations where the leaflet operating stress is lower.

It will be understood that the foregoing is only illustrative of the principles of the invention, and that various modifications can be made by those skilled in the art without departing from the scope and spirit of the invention. For example, the particular undulating shapes of the inflow and outflow valve edges that are shown herein are only illustrative, and other inflow and outflow edge shapes can be used instead if desired. As another example of possible modifications, the particular materials mentioned above for various components are only illustrative, and other materials can be used instead, if desired.

What is claimed is:

1. A prosthetic heart valve comprising:
   an annular valve-perimeter shape-defining structure having a radially outer surface;
   a clip structure on the outer surface, the clip structure having a cam which may be influenced to move the clip structure from a natural closed condition to an open condition;
   a retainer member; and
   a flexible leaflet having an edge portion that is folded over the retainer member, the retainer member and the edge portion being received in the clip structure in said open condition of said clip structure by influence on said cam, and the retainer member and the edge portion being retained in the clip structure by said cam in said closed condition of said clip structure.

2. The valve defined in claim 1 wherein the valve-perimeter-shape-defining structure includes a pair of annularly spaced commissure regions, and wherein the clip structure includes a plurality of portions that are spaced from one another along the valve-perimeter-shape-defining structure from adjacent one of the commissure regions to adjacent the other of the commissure regions.

3. The valve defined in claim 1 wherein the valve-perimeter-shape-defining structure includes a pair of annularly spaced commissure regions, and wherein the retainer member extends continuously from adjacent one of the commissure regions to adjacent the other of the commissure regions.

4. The valve defined in claim 1 wherein the valve-perimeter-shape-defining structure includes a pair of annularly spaced commissure regions, and wherein the clip structure extends more than half of the distance from adjacent one of the commissure regions to adjacent the other of the commissure regions.

5. The valve defined in claim 1 wherein the valve-perimeter-shape-defining structure includes a blood-inflow edge and a blood-outflow edge, and wherein the clip structure is open in a direction toward the blood-inflow edge and can be entered by the retainer member and the edge portion from a side of the clip structure that is toward the blood-inflow edge.

6. The valve defined in claim 1 wherein the valve-perimeter-shape-defining structure includes a blood-inflow edge and a blood-outflow edge, and wherein the leaflet extends from the clip structure, around the blood-inflow edge, and into a space that is surrounded by the valve-perimeter-shape-defining structure.

7. The valve defined in claim 1 wherein the valve-perimeter-shape-defining structure includes a blood-inflow edge and a blood-outflow edge, and wherein the clip structure is open in a direction toward the blood-outflow edge and can be entered by the retainer member and the edge portion from a side of the clip structure that is toward the blood-outflow edge.

8. The valve defined in claim 1 wherein the valve-perimeter-shape-defining structure includes a blood-inflow edge and a blood-outflow edge, and wherein the leaflet extends from the clip structure, over the blood-outflow edge, and toward an axis about which the valve-perimeter-shape-defining structure is annular.

9. The valve defined in claim 1 further comprising a cover over a radially outer surface of the clip structure.

10. The valve defined in claim 9 wherein the cover is adapted for sutures to be passed through in order to suture the valve into a patient.

11. A prosthetic heart valve comprising:
an annular valve-perimeter-shape-defining structure having a radially outer surface;
a clip structure on the outer surface, the clip structure having an open state and a closed state defined by movement of a cam element; and
a flexible leaflet having an edge portion that is at least partly secured to the valve-perimeter-shape-defining structure by being retained in the clip structure by the cam element when in said closed state.

12. The valve defined in claim 11 further comprising:
a retainer member disposed in the clip structure with the edge portion to help the clip structure retain the leaflet.

13. The valve defined in claim 12 wherein the edge portion is folded over the retainer member in the clip structure.

14. The valve defined in claim 11 wherein the valve-perimeter-shape-defining structure includes a pair of annularly spaced commissure regions, and wherein the clip structure includes a plurality of portions that are spaced from one another along the valve-perimeter-shape-defining structure from adjacent one of the commissure regions to adjacent the other of the commissure regions.

15. The valve defined in claim 11 wherein the valve-perimeter-shape-defining structure includes a pair of annularly spaced commissure regions, and wherein a retainer member extends continuously from adjacent one of the commissure regions to adjacent the other of the commissure regions.

16. The valve defined in claim 11 wherein the valve-perimeter-shape-defining structure includes a pair of annularly spaced commissure regions, and wherein the clip structure extends more than half of the distance from adjacent one of the commissure regions to adjacent the other of the commissure regions.

17. The valve defined in claim 11 wherein the valve-perimeter-shape-defining structure includes a blood-inflow edge and a blood-outflow edge, and wherein the clip structure is open in a direction toward the blood-inflow edge and can be entered by the edge portion from a side of the clip structure that is toward the blood-inflow edge.

18. The valve defined in claim 11 wherein the valve-perimeter-shape-defining structure includes a blood-inflow edge and a blood-outflow edge, and wherein the leaflet extends from the clip structure, around the blood-inflow edge, and into a space that is surrounded by the valve-perimeter-shape-defining structure.

19. The valve defined in claim 11 wherein the valve-perimeter-shape-defining structure includes a blood-inflow edge and a blood-outflow edge, and wherein the clip structure is open in a direction toward the blood-outflow edge and can be entered by the edge portion from a side of the clip structure that is toward the blood-outflow edge.

20. The valve defined in claim 11 wherein the valve-perimeter-shape-defining structure includes a blood-inflow edge and a blood-outflow edge, and wherein the leaflet extends from the clip structure, over the blood-outflow edge, and toward an axis about which the valve-perimeter-shape-defining structure is annular.

21. The valve defined in claim 11 further comprising:
a cover over a radially outer surface of the clip structure.

22. The valve defined in claim 11 further comprising:
a sewing cuff attached to an outside of at least a portion of the outer surface.

23. A method of making a prosthetic heart valve comprising:
providing an annular valve-perimeter shape-defining structure having a radially outer surface on which a clip structure is provided, the clip structure having an open condition and a closed condition, the open condition being obtained by influence on a cam surface of the clip structure;
folding an edge portion of a leaflet over a retainer member; and
inserting the edge portion and the retainer member into the clip structure against the cam surface to move the clip structure into said open condition;
securing the leaflet to the valve-perimeter-shape-defining structure when the clip structure is in the closed condition.

24. The method defined in claim 23 wherein the valve-perimeter-shape-defining structure is annular about a central longitudinal axis, wherein the valve perimeter-shape-defining structure includes first and second end edges that face away from one another in opposite directions along the central longitudinal axis, and wherein the method further comprises:
folding the leaflet over one of the end edges and inwardly of the valve-perimeter-shape defining structure toward the central longitudinal axis.

25. The method defined in claim 23 further comprising:
attaching a sewing cuff to an outside of at least a portion of the outer surface.

26. The valve defined in claim 1 wherein the clip structure is attached to the annular valve-perimeter shape-defining structure, and the clip structure has a base portion that projects radially out from the annular valve-perimeter shape-defining structure.

27. The valve defined in claim 11 wherein the clip structure is attached to the annular valve-perimeter shape-defining structure, and the clip structure has a base portion that projects radially out from the annular valve-perimeter shape-defining structure.

28. The method defined in claim 23 wherein the clip structure is attached to the annular valve-perimeter shape-defining structure, and the clip structure has a base portion that projects radially out from the annular valve-perimeter shape-defining structure.

29. The valve defined in claim 1 wherein the clip structure has a free end that projects from the base portion back toward the annular valve-perimeter shape-defining structure.

30. The valve defined in claim 11 wherein the clip structure has a free end that projects from the base portion back toward the annular valve-perimeter shape-defining structure.

31. The method defined in claim 23 wherein the clip structure has a free end that projects from the base portion back toward the annular valve-perimeter shape-defining structure.

32. The valve defined in claim 4 wherein the valve-perimeter-shape-defining structure includes a pair of annularly spaced commissure regions, and wherein the clip structure extends continuously from adjacent one of the commissure regions to adjacent the other of the commissure regions.

33. The valve defined in claim 16 wherein the valve-perimeter-shape-defining structure includes a pair of annularly spaced commissure regions, and wherein the clip structure extends continuously from adjacent one of the commissure regions to adjacent the other of the commissure regions.

* * * * *